US009052315B2

(12) United States Patent
Rodriguez et al.

(10) Patent No.: US 9,052,315 B2
(45) Date of Patent: Jun. 9, 2015

(54) RAPID DETECTION OF ANALYTES IN LIQUID SAMPLES

(71) Applicant: Advanced Animal Diagnostics, Inc., Durham, NC (US)

(72) Inventors: Rodolfo R. Rodriguez, Cary, NC (US); David A. Calderwood, Chapel Hill, NC (US)

(73) Assignee: Advanced Animal Diagnostics, Inc., Durham, NC (US)

( * ) Notice: Subject to any disclaimer, the term of this patent is extended or adjusted under 35 U.S.C. 154(b) by 0 days.

(21) Appl. No.: 13/889,744

(22) Filed: May 8, 2013

(65) Prior Publication Data

US 2013/0302788 A1 Nov. 14, 2013

Related U.S. Application Data

(60) Provisional application No. 61/644,708, filed on May 9, 2012.

(51) Int. Cl.
| | | |
|---|---|---|
| A61K 39/02 | (2006.01) |
| G01N 33/53 | (2006.01) |
| A61K 39/00 | (2006.01) |
| G01N 33/569 | (2006.01) |
| G01N 33/558 | (2006.01) |

(52) U.S. Cl.
CPC .......... *G01N 33/56933* (2013.01); *A61K 39/02* (2013.01); *G01N 33/558* (2013.01)

(58) Field of Classification Search
CPC ... A81K 39/02; A81K 39/0241; G01N 33/53; G01N 33/536; G01N 33/569; G01N 33/56933
USPC .................. 424/130.1, 184.1, 264.1; 435/7.1, 435/283.1, 297.2, 288.3, 288.4, 288.5; 436/513
See application file for complete search history.

(56) References Cited

U.S. PATENT DOCUMENTS

| | | | |
|---|---|---|---|
| 4,440,301 A | 4/1984 | Intengan |
| 4,946,266 A | 8/1990 | Kraft et al. |
| 5,132,210 A | 7/1992 | Adams et al. |
| 5,494,829 A | 2/1996 | Sandstrom et al. |
| 5,932,872 A | 8/1999 | Price |
| 6,057,166 A | 5/2000 | Childs et al. |
| 6,248,596 B1 | 6/2001 | Durst et al. |
| 6,322,963 B1 | 11/2001 | Bauer |
| 6,627,621 B2 | 9/2003 | Nagaoka et al. |
| 6,750,006 B2 | 6/2004 | Powers et al. |
| 6,790,661 B1 | 9/2004 | Goodnow |
| 7,390,997 B2 | 6/2008 | Tohma |
| 7,566,533 B2 | 7/2009 | Jacobs et al. |
| 7,589,962 B1 | 9/2009 | Bhatia |
| 7,855,051 B2 | 12/2010 | Anderson et al. |
| 7,861,768 B1 | 1/2011 | Ghantiwala |
| 7,898,673 B2 | 3/2011 | Randers-Pehrson et al. |
| 7,932,093 B2 | 4/2011 | Renuart et al. |
| 7,943,153 B1 | 5/2011 | Leonard et al. |
| 8,021,848 B2 | 9/2011 | Straus |
| 8,067,246 B2 | 11/2011 | Marlborough et al. |
| 2001/0036645 A1 | 11/2001 | McNeirney et al. |
| 2002/0098588 A1 | 7/2002 | Sammak et al. |
| 2003/0127609 A1 | 7/2003 | El-Hage et al. |
| 2003/0206296 A1 | 11/2003 | Wolleschensky et al. |
| 2004/0101826 A1 | 5/2004 | Jones et al. |
| 2004/0101912 A1 | 5/2004 | Rubin et al. |
| 2004/0115624 A1 | 6/2004 | Wolde-Mariam |
| 2004/0208350 A1 | 10/2004 | Rea et al. |
| 2005/0260695 A1 | 11/2005 | Fleming et al. |
| 2006/0068412 A1 | 3/2006 | Tang et al. |
| 2006/0134796 A1 | 6/2006 | Bommarito et al. |
| 2007/0015151 A1 | 1/2007 | Schrenzel et al. |
| 2007/0190566 A1 | 8/2007 | Montagu |
| 2007/0242349 A1 | 10/2007 | Tafas |
| 2007/0287147 A1 | 12/2007 | Nagamune et al. |
| 2008/0088918 A1 | 4/2008 | O'Connell |
| 2008/0220539 A1 | 9/2008 | Brauner et al. |
| 2008/0259566 A1 | 10/2008 | Fried |
| 2009/0042814 A1 | 2/2009 | Petyaev et al. |

(Continued)

FOREIGN PATENT DOCUMENTS

| | | |
|---|---|---|
| EP | 1 975 618 A1 | 10/2008 |
| JP | 2011-004654 A | 1/2011 |

(Continued)

OTHER PUBLICATIONS

Anderson et al. "Fresh cow mastitis monitoring on day 3 postpartum and its relationship to subsequent milk production", *Journal of Dairy Science*, Dec. 2010, vol. 93, No. 12, 5673-5683.

Ball et al. "An Antigen Capture ELISA Test using Monoclonal Antibodies for the Detection of *Mycoplasma californicum* in Milk", *Veterinary Immunology and Immunopathology*, 1990, vol. 25, 269-278.

Boothby et al. "Detecting *Mycoplasma bovis* in milk by enzyme-linked immunosorbent assay, using monoclonal antibodies", *American Journal of Veterinary Research*, 1986, 47(5):1082-1084.

Cimolai et al. "Culture-amplified Immunological Detection of *Mycoplasma pneumoniae* in Clinical Specimens", *Diagn Microbiol Infect Dis.*, 1988;9:207-212.

Elert et al. Diameter of a Yeast, The Physics Factbook, 2000, Retrieved from the internet on Nov. 22, 2013 at URL http://hypertextbook.com/facts/2000/JennyNg.shtml.

(Continued)

*Primary Examiner* — Rodney P Swartz
(74) *Attorney, Agent, or Firm* — Myers Bigel Sibley & Sajovec, P.A.

(57) ABSTRACT

A device for detecting at least one analyte (and in some embodiments two, three, or four or more different analytes) in a liquid sample generally comprises (i) a support having a chamber for receiving a biological fluid therein, wherein said chamber is an elongate chamber having a length axis; (ii) a carrier or agitator in said elongate chamber, said carrier or agitator having opposite end portions and a side portion, the carrier or agitator dimensioned to travel in said chamber along said length axis and/or permit said liquid sample to flow in the chamber therearound, either (or both) thereby agitating the liquid sample; and (iii) at least one anti-analyte antibody coupled to either the carrier and/or the chamber side wall.

23 Claims, 3 Drawing Sheets

(56) References Cited

U.S. PATENT DOCUMENTS

| | | | |
|---|---|---|---|
| 2009/0068759 | A1 | 3/2009 | Arenas et al. |
| 2009/0116101 | A1 | 5/2009 | Tafas et al. |
| 2009/0233329 | A1 | 9/2009 | Rodriguez et al. |
| 2010/0118394 | A1 | 5/2010 | Hecker |
| 2010/0135861 | A1 | 6/2010 | Sage et al. |
| 2010/0210022 | A1 | 8/2010 | Madura |
| 2010/0227333 | A1 | 9/2010 | Horowitz |
| 2010/0254854 | A1 | 10/2010 | Rich et al. |
| 2010/0255601 | A1 | 10/2010 | Beaudet et al. |
| 2010/0279310 | A1 | 11/2010 | Sia et al. |
| 2010/0328766 | A1 | 12/2010 | Griffin et al. |
| 2011/0003310 | A1 | 1/2011 | Ennis et al. |
| 2011/0090326 | A1 | 4/2011 | Kenny et al. |
| 2011/0117025 | A1 | 5/2011 | Dacosta et al. |
| 2012/0082361 | A1 | 4/2012 | Burke et al. |

FOREIGN PATENT DOCUMENTS

| | | |
|---|---|---|
| WO | WO 2004/097412 | 11/2004 |
| WO | WO 2008/002563 A2 | 1/2008 |
| WO | WO 2008/021862 | 2/2008 |
| WO | WO 2009/013683 | 1/2009 |
| WO | WO 2009/105711 | 8/2009 |
| WO | WO 2010/013335 A1 | 2/2010 |
| WO | WO 2012/051372 | 4/2012 |
| WO | WO 2012/094625 | 7/2012 |

OTHER PUBLICATIONS

Fedorko et al. "Evaluation of a Rapid Enzyme Immunoassay System for Serologic Diagnosis of *Mycoplasma pneumoniae* Infection", *Diagn Microbiol Infect Dis.*, 1995;23:85-88.

Fischer J.E. et al. "Autofokus zur schnellen Verarbeitung mikroskipischer Praeparate", Informatik Fachberichte—Mustererkennung 1991, 13, DAGM Symposium Proceedings, Munchen, Oct. 9-11, 19991, vol. 290, Oct. 9, 1991, pp. 367-372.

Geusebroek et al. "Robust autofocusing in microscopy", Cytometry, vol. 39, Feb. 2000, pp. 1-9.

Heller et al. "Antigen capture ELISA using a monoclonal antibody for the detection of *Mycoplasma bovis* in milk", *Veterinary Microbiology*, 1993, 37:127-133.

International Search Report and Written Opinion Corresponding to International Application No. PCT/US2013/049112; Date of Mailing: Dec. 13, 2013; 12 Pages.

International Search Report and Written Opinion Corresponding to International Application No. PCT/US2013/049247; Date of Mailing: Dec. 5, 2013; 13 Pages.

International Search Report and Written Opinion Corresponding to International Application No. PCT/US2013/040372; Date of Mailing: Jul. 16, 2013; 9 Pages.

International Search Report and Written Opinion Corresponding to International Application No. PCT/US2013/040379; Date of Mailing: Sep. 5, 2013; 14 Pages.

International Search Report and Written Opinion Corresponding to International Application No. PCT/US2013/040382; Date of Mailing: Dec. 6, 2013; 17 Pages.

Kok et al. "Routine diagnosis of seven respiratory viruses and *Mycoplasma pneumoniae* by enzyme immunoassay", *Journal of Virological Methods*, 1994, 50:87-100.

Madsen et al. "The simultaneous direct detection of *Mycoplasma pneumoniae* and Legionella pneumphila antigens in sputum specimens by a monoclonal antibody immunoblot assay", *Journal of Immunological Methods*, 1987, 103:205-210.

Martinez et al. "Immunobinding Assay for Detection of *Mycoplasma bovis* in Milk", *Can J Vet Res*, 1990; 54:251-255.

Miettinen et al. Detection of *Mycoplasma hominis* Antigen in Clinical Specimens by Using a Four-Layer Modification of Ezyme Immunoassay (EIA), *Journal of Immunological Methods*, 1984, 69:267-275.

Molecular Devices, Multi Dimensional Acquisition: Auto Focus Dialog, Molecular Devices Article #T20125, Aug. 27, 2009, Retrieved from the internet on Nov. 22, 2013 at URL http://support.meta.moleculardevices.com/docs/t20125.pdf.

Talkington et al. "Analysis of Eight Commercial Enzyme Immunoassay Tests for Detection of Antibodies to *Mycoplasma pneumoniae* in Human Serum" *Clin. Diagn. Lab. Immunol.*, 2004, 11(5):862.

Tuuminen et al. "Improved sensitivity and specificity of enzyme immunoassays with P1-adhesin enriched antigen to detect acute *Mycoplasma pneumoniae* infection", *Journal of Microbiological Methods*, 2001, 44:27-37.

Uldum et al. "Enzyme Immunoassay for Detection of Immunoglobulin M (IgM) and IgG Antibodies to *Mycoplasma pneumoniae*", *Journal of Clinical Microbiology*, May 1992, vol. 30, No. 5, pp. 1198-1204.

Xiao, Yan, and Siugong Gao. "Use of IgY antibodies and semiconductor nanocrystal detection in cancer biomaker quantitation", Biomakers in Medicine, (2010), 4;2:224-239.

RAPID DETECTION OF ANALYTES IN LIQUID SAMPLES

RELATED APPLICATIONS

This application claims the benefit of U.S. Provisional Patent Application Ser. No. 61/644,708, filed May 9, 2012, the disclosure of which is incorporated by reference herein in its entirety.

FIELD OF THE INVENTION

The present invention concerns methods and apparatus for detecting analytes, including pathogens such as *Mycoplasma* species, in liquid samples such as biological fluids.

BACKGROUND OF THE INVENTION

The *Mycoplasma* are a wide-spread group of bacteria. Species such as *M. pneumonia* and *M. genitalium* cause disease in humans. Related species cause disease in plants. *M. bovis* is considered one of the more pathogenic species and causes pneumonia, mastitis, and arthritis in cattle. In research laboratories, *Mycoplasma* species are frequent contaminants in cell cultures.

*Mycoplasma* are characterized by the absence of a cell wall. Unfortunately, the most important group of antibiotics, the beta-lactams (which include both the penicillins and the cephalosporins) function by inhibiting cell wall synthesis. With important antibiotics such as these unavailable for the treatment of *Mycoplasma* infections, there is a need for new and rapid methods and apparatus for the detection of these species so that they may be quickly detected on occurrence and controlled or eradicated before the spread thereof.

SUMMARY OF THE INVENTION

A first aspect of the invention is a device for detecting at least one analyte (and in some embodiments two, three, or four or more different analytes) in a liquid sample. The device generally comprises (i) a support having a chamber for receiving a biological fluid therein, wherein said chamber is an elongate chamber having a length axis; (ii) a carrier or agitator in said elongate chamber, said carrier or agitator having opposite end portions and a side portion, the carrier or agitator dimensioned to travel in said chamber along said length axis and/or permit said liquid sample to flow in the chamber therearound, thereby agitating the liquid sample; and (iii) at least one anti-analyte antibody coupled to either the carrier and/or the chamber side wall. In some embodiments, the carrier is or agitator is configured so as to bring analytes into sufficiently close physical proximity with their corresponding antibody to cause binding of the antibody to its corresponding analyte, thereby obviating the need to rely upon simple diffusion of analyte in the sample to the antibody for binding.

When a plurality (e.g., two, three, four or more) different antibodies are bound to the carrier and/or chamber side wall, each of which binds a different analyte, they are preferably bound at separate and discrete locations on the carrier and/or chamber side wall portion.

A second aspect of the invention is a method of quantitatively or qualitatively detecting an analyte (or in some embodiments two or more different analytes) in a liquid sample. The method is carried out by (a) providing a device as described herein; (b) adding the liquid sample to the chamber; (c) agitating the support in the liquid sample within the chamber sufficient to bind analyte in said liquid sample to the antibody; and then (d) detecting the presence or absence of binding of the one or more analyte to its respective antibody. Quantitative detection can be carried out by any suitable technique, such as manual or automated microscopy (e.g., fluorescence or epifluorescent microscopy) of cells or pathogens bound by the antibody.

Detection of analyte bound to the respective antibodies may be carried out by any suitable technique, including but not limited to cell staining, immunoassay, radioassay, fluorescent assay, enzyme assay, ultraviolet illumination, optical microscopy, etc., including combinations thereof.

U.S. Pat. No. 5,776,710 to Levine et al. describes a method and apparatus for assaying analytes such as CD-4 cells, but generally relies on separation or concentration of cells by centrifugation, and is not adapted to the concurrent detection of multiple analytes.

While the present invention is concerned in one embodiment with the detection of *Mycoplasma*, it will be appreciated that the invention can also be applied to numerous additional analytes, as discussed further below.

The present invention is explained in greater detail in the drawings herein and the specification set forth below. The disclosures of all United States Patent references cited herein are to be incorporated by reference herein in their entirety.

DETAILED DESCRIPTION OF THE PREFERRED EMBODIMENTS

Figure 1:
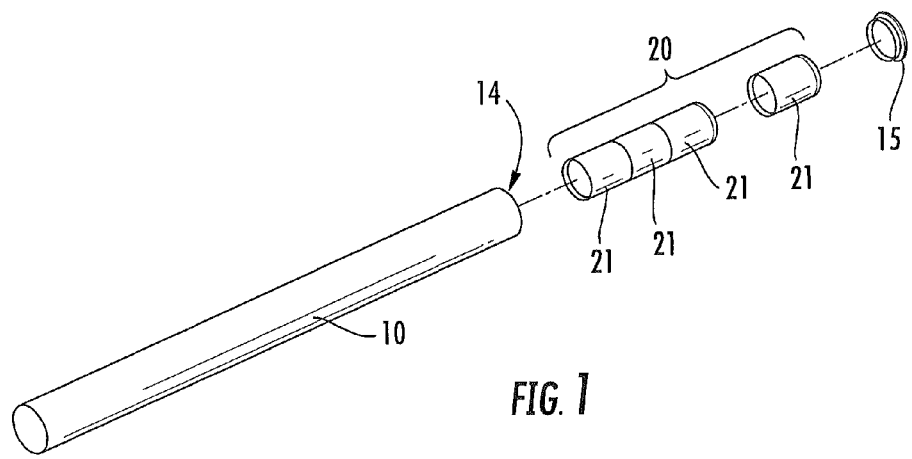
FIG. 1 is an exploded perspective view of a first embodiment of the invention.

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

1. DEFINITIONS

"Subject" as used herein includes both human and animal subjects for veterinary purposes, as well as plants for agricultural purposes. Examples of animal subjects include, but are not limited to, mammalian subjects such as dog, cat, cow, sheep, goat, horse, and pig subjects, fish such as salmon, trout, and tilapia, and avian subjects such as chicken, turkey, duck, geese, quail, and pheasant.

"Liquid sample" as used herein may be any liquid suspected of containing one or more analytes. The liquid sample is typically an aqueous sample, and may be provide as a a single phase or multi-phase sample (e.g., an emulsion, dispersion, or suspension of solid or liquid particles in a (typically aqueous) continuous phase). For example: plant or animal tissue, or a solid food sample, may be homogenized in an aqueous solution to provide a liquid sample; a solid sample such as a soil sample may be rinsed in an aqueous rinse or wash solution such as water or buffer solution, and the rinse or wash solution used as the aqueous sample. A water sample may be taken from a pond, ocean, stream, river or the like, optionally diluted, and used as the liquid sample. In some embodiments, the liquid sample is a biological fluid. In some embodiments the liquid sample is a growth media such as cell or tissue culture media.

"Biological fluid" as used herein refers to a liquid solution or suspension comprising material collected from or excreted by a subject. Examples include, but are not limited to, milk, whole blood, blood plasma, urine, lymph, nasal swab, sputum, bronchial lavage fluid, etc., from human and animal subjects; sap, nectar or juice from plants, tissue homogenates of any thereof, and fractions of any thereof such as blood plasma. The fluid may be taken from a vector such as an insect that carries the pathogen, or may comprise a tissue homogenate of such vector. The biological fluid may further comprise or contain one or more additives such as diluents (e.g., aqueous diluents such as saline solutions), anticoagulants, preservative, salts, buffers, etc.

"Milk" as used herein generally refers to mammalian milk of any species (e.g., cow, goat, human, etc.). The milk may be raw or pasteurized, depending upon the particular purpose of the test. Milk may be whole milk, low-fat or reduced fat milk, or skim milk. Milk may optionally be diluted (typically with an aqueous diluent such as distilled water, saline solution, or buffer solution).

"Analyte" (also referred to as "measurands") as used herein includes any suitable target of analysis or target of measurement. Such analytes, measurands, or targets as used herein may be any suitable compound or cell to which an antibody will bind, including but not limited to proteins, peptides, nucleic acids, toxins, and pathogens. "Toxin" as used herein includes, but is not limited to, mycotoxins and bacterial toxins (e.g., exotoxins, enterotoxins, and/or endotoxins).

"Mycotoxin" as used herein includes, but is not limited to, aflatoxins (e.g., aflatoxin B1, B2, G1, and G2), vomitoxin, ochratoxins (e.g., ochratoxin A, B, and C), citrinin, ergot alkaloids, and *fusarium* toxins (e.g., fumonisins, and trichothecenes).

"Enterotoxin" as used herein includes, but is not limited to, *Staphylococcus aureus* enterotoxin and *Escherichia coli* enterotoxin.

"Pathogen" as used herein may be any pathogen, including viral, fungal (including yeast), bacterial (including Gram negative and Gram positive bacteria), and protozoan pathogens. In some embodiments, the pathogen is a mollicute such as a *mycoplasma*.

"Mollicute" as used herein refers to a class of bacteria characterized by the absence of a cell wall. Orders within the class Molicutes include Acholeplasmatales, Anaeroplasmatales, Entomoplasmatales, Haloplasmatales, and Mycoplasmatales. Examples include, but are not limited to *Mycoplasma, Ureaplasma, Acholeplasma, Spiroplasma,* and *Phytoplasma*.

"*Mycoplasma*" as used herein refers to a genera of bacteria within the order Mycoplasmatales that lack a cell wall. Examples include, but are not limited to, *Mycoplasma bovis, Mycoplasma genitalium, Mycoplasma hominis, Mycoplasma hyopneumoniae, Mycoplasma laboratorium, Mycoplasma ovipneumoniae, Mycoplasma pneumonia, Mycoplasma haemofelis,* etc.

"Antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26, 403-11 (1989). The antibodies may be recombinant monoclonal antibodies produced according to the methods disclosed in Reading, U.S. Pat. No. 4,474,893, or Cabilly et al., U.S. Pat. No. 4,816,567. Antibody fragments included within the scope of the present invention include, for example, Fab, F(ab')2, and Fc fragments, and the corresponding fragments obtained from antibodies other than IgG. Such fragments can be produced by known techniques.

2. ANTIBODIES AND ANALYTES FOR DETECTION

As noted above, the present invention may be utilized for detecting any of a variety of analytes to which antibodies may be raised, and to which antibodies bind. In some embodiments, the analyte is, or the analytes are, pathogens or toxins.

Numerous pathogens are known. See, e.g., U.S. Pat. No. 7,945,393. Examples of pathogens (e.g., human pathogens or those of animals or plants) that can be assessed using the methods described herein include bacteria (including eubacteria and archaebacteria), eukaryotic microorganisms (e.g., protozoa, fungi, yeasts, and molds) viruses, and biological toxins (e.g., bacterial or fungal toxins or plant lectins). Specific examples of such pathogens include protozoa of the genus *Cryptosporidium*, protozoa of the genus *Giardia*, bacteria of genera such as *Escherichia, Escherichia coli, Escherichia coli* 157, *Yersinia, Francisella, Brucella, Clostridium, Burkholderia, Chlamydia, Coxiella, Rickettsia, Vibrio, Leptospira, Enterococcus, Staphylococcus, Streptococcus,* methicillin-resistant *Staphylococcus* (MRSA), *Enterobacter, Corynebacterium, Pseudomonas, Acineto-* bacter, Klebsiella, and Serratia. Assessable organisms include at least Escherichia coli, Yersinia pestis, Francisella tularensis, Clostridium perfringens, Burkholderia mallei, Burkholderia pseudomallei, cryptosporidia microorganisms, Francisella tularensis (Tularemia), Brucella species (Brucellosis), Chlamydia psittaci (Psittacosis), Coxiella burneti (Q fever), Rickettsia prowazeki (Typhus fever), Vibrio vulnificus, Vibrio enteralyticus, Vibrio fischii, Vibrio cholera, Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens, Candida albicans, Microsporum audouini, Microsporum canis, Microsporum gypseum, Trichophyton mentagrophytes var. mentagrophytes, Trichophyton mentagrophytes var. interdigitale, Trichophyton rubrum, Trichophyton tonsurans, Trichophyton verrucosum, and Epidermophytum floccosum, Streptococcus (including Strep A, B, C, G) Filoviruses such as Ebola and Marburg viruses, Naviruses such as Lassa fever and Machupo viruses, Alphaviruses such as Venezuelan equine encephalitis virus, Eastern equine encephalitis virus, and Western equine encephalitis virus, Rotaviruses, Calciviruses such as Norwalk virus, and Hepatitis (A, B, and C) viruses.

Additional examples of pathogens that can be detected by the methods and apparatus of the present invention include, but are not limited to, Bacillus anthracis, Bartonella quintana, Brucella melitensis, Burkholderia mallei, Burkholderia pseudomallei, Chlamydia psittaci, Clostridium botulinum, Clostridium perfringens, Coxiella burnetti, enterohemorrhagic Escherichia coli, Francisella tularensis, Rickettsia mooseri, Rickettsia prowasecki, Rickettsia rickettsii, Rickettsia tsutsugamushii, Salmonella typhi, Salmonella, Shigella, Shigella dysenteriae, Vibrio cholerae, Yersinia pestis, Coccidioides immitis, Histoplasma capsulatum, chikungunya virus, Congo-Crimean haemorrhagic fever virus, dengue fever virus, Eastern equine encephalitis virus, Ebola virus, Equine morbillivirus, Hantaan virus, Japanese encephalitis virus, Junin virus, Lassa fever virus, Epstein Barr virus (infectious mononucleosis), Lymphocytic choriomeningitis virus, Machupo virus, Marburg virus, Monkey pox virus, Murray valley encephalitis virus, Nipah virus, Omsk hemorrhagic fever virus, Oropouche virus, Rift valley fever virus, Russian Spring-Summer encephalitis virus, smallpox virus, South American hemorrhagic fever viruses, St. Louis encephalitis virus, tick-borne encephalitis virus. Variola virus, Venezuelan equine encephalitis virus, Western equine encephalitis virus, White pox virus, Yellow fever virus, Botulinum toxins, Clostridium perfringens toxins, microcystins (Cyanginosins), Shiga toxin, verotoxin, Staphylococcal enterotoxin B, anatoxin A, conotoxins, palytoxin, saxitoxin, tetrodotoxin, stachybotrys toxins, aflatoxins, trichothecenes, satratoxin H, T-2 toxin, and ricin. Other examples include Abrus precatorius lectin, African swine fever virus, Avian influenza virus, Banana bunchy top virus, Bluetongue virus, Camelpox virus, Cholera toxin, Clostridium perfringens, Clostridium tetani, Cryptosporidium parvum, Deuterophoma tracheiphila, Entamoeba histolytica, ergot alkaloids, Escherichia coli 0157, Foot and mouth disease virus, Giardia, Giardia lamblia, Goat pox virus, Hendra virus, Hepatitis A virus, Hog cholera virus, Human immunodeficiency virus, Infectious conjunctivitis virus, Influenza virus (including Influenza A, Influenza B, and Influenza C viruses), Kyasanur Forest virus, Legionella pneumophila, Louping ill virus, Lyssaviruses, Adenia digitata lectin (modeccin), Monilia rorei, Naegleria fowleri, Nipah virus, Murray Valley encephalitis virus, Mycoplasma mycoides, Newcastle disease virus, Oropouche virus, Peste des petits ruminants virus, Porcine enterovirus 9, Powassan virus, Pseudorabies virus, Rinderpest virus, Rocio virus, Group B rotaviruses, Salmonella paratyphi, Sheeppox virus, St. Louis encephalitis virus, substance P, Serratia marcescens, Teschen-Talfan virus, tetanus toxin, Vesicular stomatitis virus, Visctim album lectin 1 (Viscumin), Adenia volkensii lectin (volkensin), West Nile virus, Xanthomonas campestris oryzae, Xylella fastidiosa, and Yersinia pseudotuberculosis.

Examples of plant pathogens that can be assessed by the methods and apparatus of the present invention include, but are not limited to, Burkholderia solanacearum, Citrus greening disease bacteria, Erwinia amylovora, Xanthomonas albilineans, Xanthomonas axonopodis pv. citri, Bipolaris (Helminthosporium) maydis, Claviceps purpurea, Colletotrichum coffeanum virulans, Cochliobolus miyabeanus, Dothistroma pini, Fusarium oxysporum, Microcystis ulei, Neovossia indica, Peronospora hyoscyami, Puccinia erianthi, Puccinia graminis, Puccinia graminis f sp. tritici, Puccinia striifonnis, Pyricularia grisea, Sclerotinia scierotiorum, Sclerotium rolfsii, Tilletia indica, Ustilago maydis, Phytophthora infestans, and Fiji disease virus.

In some embodiments, the pathogen is detected directly. In other embodiments, the pathogen is indirectly detected by detecting the presence of a toxin which the antibody produces, whether or not the pathogen itself remains present.

Polyclonal antibodies used to carry out the present invention may be produced by immunizing a suitable animal (e.g., rabbit, goat, etc.) with an antigen (e.g., the analyte, optionally coupled to an adjuvant), collecting immune serum from the animal, and separating the polyclonal antibodies from the immune serum, in accordance with known procedures. Monoclonal antibodies used to carry out the present invention may be produced in a hybridoma cell line according to the technique of Kohler and Milstein, Nature 265, 495-97 (1975). For example, a solution containing the appropriate antigen may be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity. Monoclonal Fab fragments may be produced in Escherichia coli by recombinant techniques known to those skilled in the art. See, e.g., W. Huse, Science 246, 1275-81 (1989). Antibodies specific to the analyte may also be obtained by phage display techniques known in the art.

Once produced, the antibody is immobilized on a solid support in the appropriate region or location in the apparatus described below (e.g., on the carrier, on the chamber wall) in accordance with known techniques or variations thereof that will be apparent to those skilled in the art. See, e.g., U.S. Pat. Nos. 8,101,155; 8,043,821; 8,003,766; 7,829,294; 7,695,609; 7,288,253; and 7,247,453.

3. APPARATUS

Figure 2:
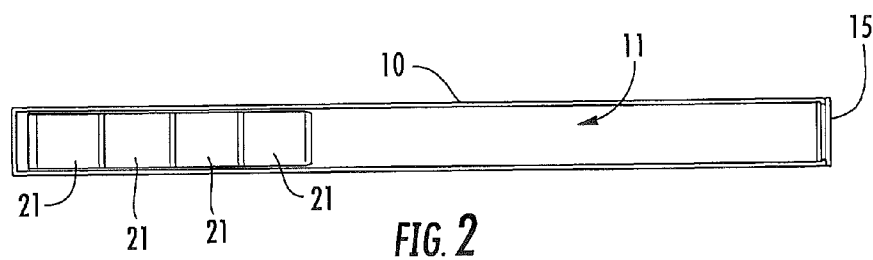
FIG. 2 is a side sectional view of the embodiment of FIG. 1.

As noted above, the present invention provides a device for detecting at least one analyte in a liquid sample. As illustrated in FIGS. 1-2, the device may generally comprise: (a) a support 10 having a chamber 11 for receiving a liquid sample therein, wherein said chamber is an elongate chamber having a length axis. A carrier or agitator 20 is disposed in the elongate chamber, the carrier having opposite end portions and a side portion, with carrier dimensioned to travel in the chamber along said length axis. At least one anti-analyte antibody is coupled to the carrier (e.g., at a side portion, end portion or internal pore, channel, or chamber), and/or to the chamber interior side wall portion. A port 14 is covered by a removable end cap 15 so that a liquid sample can be inserted into the chamber.

Figure 3:
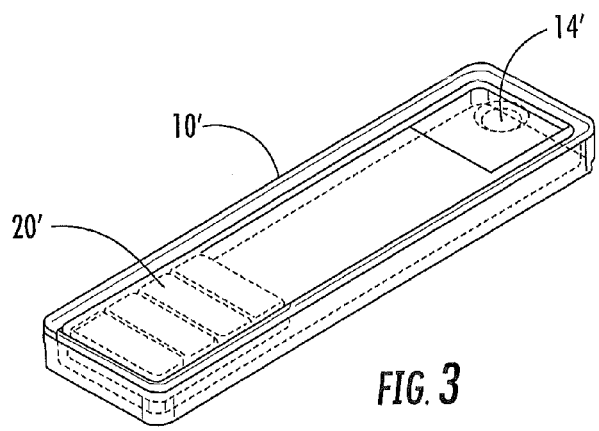
FIG. 3 is a perspective view of a second embodiment of the invention.
Figure 4:
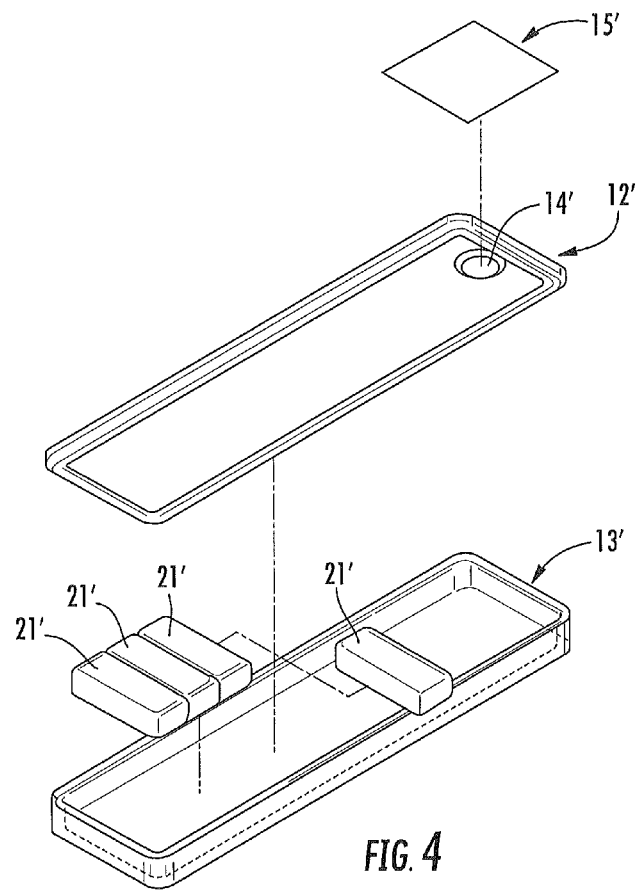
FIG. 4 is an exploded, perspective view of the embodiment of FIG. 3.
Figure 5:
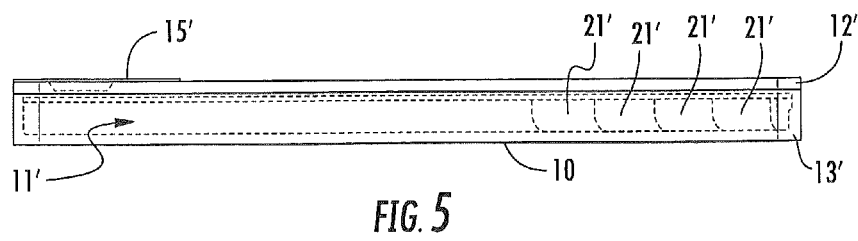
FIG. 5 is a side sectional view of the embodiment of FIG. 3.

In some embodiments, and as illustrated, the carrier 20 comprises a plurality of segments 21 connected coupled to one another, each of said segments having a side (or top) portion, with each of the side portions having a different antibody bound or coupled thereto, so that the presence of multiple different analytes in the liquid sample (e.g., four distinct analytes) may be detected An alternate, flat/planar, embodiment is shown in FIGS. 3-5, with like elements having like numbers assigned thereto. In this embodiment the support 10' defining chamber 11' is formed from an upper portion 12' and a lower portion 13'. The port 14' is formed in one end of the upper portion, and is sealed by an adhesive film 15'. The carrier 20' is again formed of a plurality of segments 21' connected to one another. When the support upper surface is optically transparent, this generally planar configuration is more suitable for quantitative determination of cellular analytes such as pathogens, which can then be detected/observed and counted by manual or automated microscopy.

The carrier or agitator may take any suitable form, including a round bead having antibody coupled to the entire surface thereof. However, as noted above, in some embodiments, the carrier or agitator 20, 20' comprises a plurality of segments 21, 21. In some embodiments, the plurality of segments comprises a pair of opposite end terminal segments and optionally at least one intermediate segment positioned therebetween, with each of said terminal segments fastened to intermediate segments by techniques such as heat staking, snap-fits, screw threads, etc.) In some embodiments, the carrier can further comprise an elongate core, with each of the plurality of segments having a transverse opening formed therein, and with each of said plurality of segments received on said core with said core extending through said transverse openings. In some embodiments, the carrier or agitator is magnetic, paramagnetic, or magnetizable (e.g., by inclusion of metal particles therein), to facilitate agitation as discussed further below. In some embodiments the carrier has a density greater than, or less than, the liquid sample for which the device is intended, so that the carrier or agitator sinks or floats in the liquid sample to facilitate agitation thereof.

Figure 6:
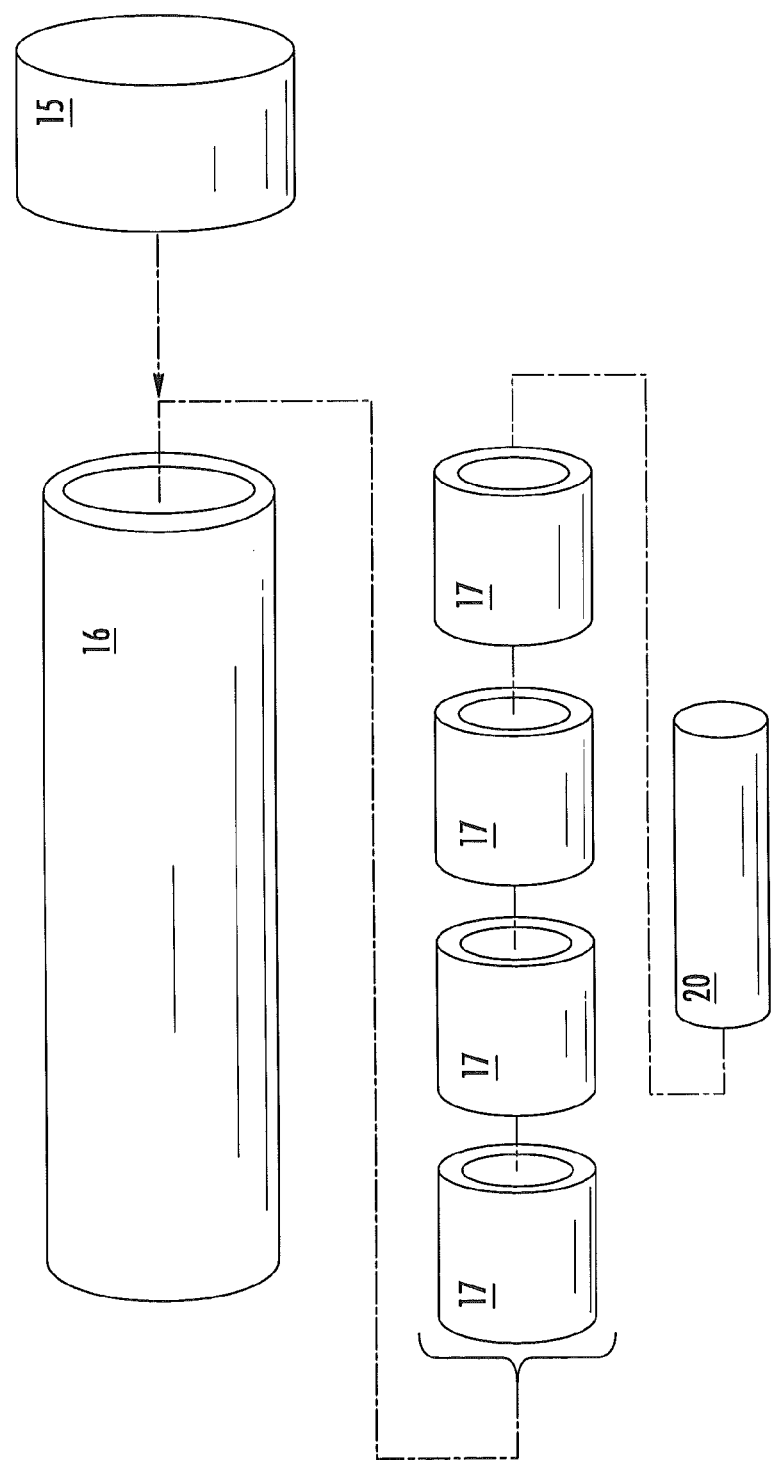
FIG. 6 is an exploded perspective view of a third embodiment of the invention.

In a still further embodiment illustrated in FIG. 6, the internal agitator is a single unitary part and does not carry any antibody. Instead, the chamber-forming support is provided as a plurality of chamber segments 16, which are nested together to form the internal chamber, through which the agitator 20 moves. As illustrated, the segments may be in the form of short cylinders (though it will be appreciated that other geometric forms, such as regular or irregular triangular, rectangular, pentagonal, etc., may also be utilized). Each segment 16 has an internal wall segment, to which different antibody may be bound. Spacer or "dummy" segments may optionally be provided. All of the segments may be disposed within an outer sleeve 17 to contain the liquid sample therein, with a cap 15 or other suitable sealing means such as an adhesive polymer film provided to contain liquid sample within the container.

In still another embodiment (not illustrated), the carrier or agitator is fixed, held, or restrained, by fastener or simply configuring the carrier to at least partially engage the chamber side wall, so that it the carrier or agitator is substantially stationary in the chamber. Agitation of the liquid sample by the carrier or agitator is, in this embodiment, achieved by passing the liquid sample around and the carrier.

In the foregoing, the support (or agitator) and/or the chamber may be transparent or opaque depending on the particular technique used to detect binding of the analyte to the antibody. In general, both the support and the chamber are composed of an organic polymer, such as polystyrene or polycarbonate.

Any suitable antibody can be used to carry out the present invention, and coupling of the antibody to the carrier can be carried out in accordance with known techniques as noted above. Antibody affinity and amount are selected to achieve the desired level of sensitivity or detectable capture of pathogens, depending upon other variables such as agitation time and technique, as discussed further below.

In some embodiments, the at least one antibody comprises an anti-bacterial pathogen antibody; In some embodiments, the at least one antibody comprises an anti-*Mycoplasma* antibody; In some embodiments, the at least one antibody comprises an anti-*Staphylococcus aureus* antibody; In some embodiments, the at least one antibody comprises at least one antibody that binds to Gram negative bacteria and at least one antibody that binds to Gram positive bacteria. In some embodiments, the at least one antibody comprises an anti-toxin antibody; In some embodiments, one of said segments carries an anti-*Mycoplasma bovis* monoclonal antibody, and another of said segments carries an anti-*Staphylococcus aureus* monoclonal antibody; In some embodiments, two, three or four or more of the foregoing features are included in combination in the apparatus so that multiple different analytes are detected.

As noted, in some embodiments, the chamber has a length dimension and said carrier has a length dimension, wherein said chamber length dimension is at least twice (and preferably three or four times) that of said carrier length dimension In some embodiments, the chamber has a width dimension and said carrier has a width dimension, wherein said chamber width dimension is from 10 to 30 percent greater than said carrier width dimension In some embodiments, the chamber has a depth dimension and said carrier has thickness dimension, wherein said chamber depth dimension is from 10 to 30 percent greater than said carrier thickness dimension.

In some embodiments, the carrier and the chamber are configured so that said carrier cannot rotate in said chamber. In general, shapes that are irregular or nonspherical in cross-section may be used to achieve this result, including but not limited to triangular, rectangular, and other polygonal, compound, or irregular cross-sectional shapes.

In some embodiments, the chamber has a total volume of from 1 ml to 10 ml, and said carrier occupies from 20 to 40 percent of the chamber volume.

The space or distance between the carrier (specifically, carrier surfaces having antibody immobilized therein) and the chamber inner wall portion is so dimensioned as to achieve the desired level of contact of pathogens potentially carried by the biological fluid over the time period of the particular agitation procedure used. In some embodiments, the spacing or distance between these two surfaces is (on average) at least 20, 30 or 40 microns, up to 200, 300, or 400 microns. It will be appreciated that irregularities can be formed (such as lips, blocks, bumps, or other texture) can be formed on either or both surface portions as a way to enhance turbulence of the biological fluid during agitation to increase the probability of pathogen carried by the biological fluid being bound by antibodies immobilized on the carrier. In some embodiments, this geometry or configuration serves to insure or enhance the probability that the analyte(s) of interest will come sufficiently close to their corresponding antibody that they are specifically bound or "captured" thereby. For example, in the embodiments of FIGS. 1-6, when the carrier or agitator is driven by gravity (sinking, or floating, in the liquid sample) and the analytes are *mycoplasma* pathogens, the pressure differential that is created from the top of the carrier to the bottom of the carrier forces a liquid sample that contains very few pathogens and many other potential analytes that are not of interest up the space or annulus between carrier/agitator and the elongated chamber, very close to the antibody, increasing the probability of capture. For *mycoplasma* pathogens in milk, where the pathogens are potentially present in small numbers, or as a rare event (e.g., 100 *mycoplasma* organisms in a fluid containing millions of white cells and billions of fat globules), this feature is particularly important.

4. METHODS OF USE

As noted above, methods of the invention are carried out by (a) providing a device as described herein; (b) adding the liquid sample to said chamber; (c) agitating the support in the liquid sample within the chamber sufficient to bind pathogen in said biological fluid to said anti-pathogen antibody; and then (d) detecting the presence or absence of binding of the pathogen to the antibody.

Agitation may be achieved by any suitable manual or automated technique that imparts motion of the carrier relative to the biological fluid, or vice versa. In contrast to the centrifugation used to concentrate and separate the carrier as described in U.S. Pat. No. 5,776,710 to Levine et al., agitation in the present invention is carried out in a manner which mixes or disperses the sample, and more particularly or mixes or disperses the analyte throughout the liquid s sample. The carrier may be moved by gravity (e.g., sink or float) as the chamber is repeatedly repositioned; the carrier may be held stationary while the chamber, and hence the fluid, is repositioned, and combinations thereof. Agitation is typically carried out at ambient or room temperature, and may be carried out for any suitable time. In some embodiments, agitation is carried out for a time of 10, 20 or 30 minutes, up to 1, 2 or 3 hours, or more.

In the alternative, as noted above, the carrier or agitator may be held, secured or positioned substantially stationary in the chamber (with constrained regions for flow of the liquid sample formed between the carrier and the chamber wall), and agitation of the liquid sample by the carrier or agitator achieved by reciprocally or continuously pumping, forcing, or flowing the liquid sample around and past the carrier (e.g., by application of a syringe, peristaltic pump, rolling chamber, gravity flow, shaking, or the like). The carrier or agitator forms constrained flow regions within the chamber that agitate by imparting shear forces and/or turbulence to the liquid sample, thus obviating the need for physically moving the carrier within the chamber when motion is imparted to the liquid sample by other means.

In some embodiments, the carrier may be magnetic or comprise a paramagnetic material, so that agitation of the carrier can be carried out by application of a magnetic field. In other embodiments, agitation may be carried out by placing the device on a rocker, roller, shaker, or other suitable agitation device.

Those skilled in the art will be familiar with numerous specific quantitative and qualitative detection and assay formats and variations thereof which may be useful for carrying out the method disclosed herein. See generally E. Maggio, Enzyme-Immunoassay, (1980)(CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." Applicants specifically intend that the disclosures of all U.S. Patent references cited herein be incorporated herein by reference in their entirety In some embodiments, the methods and device achieve detectable capture of analytes such as *Mycoplasma bovis* or *Staphylococcus aureus* present in a biological fluid such as milk at a concentration of as little as $10^2$ pathogens per milliliter of biological fluid after one hour of agitation.

The present invention is explained in greater detail in the following non-limiting Examples.

Example 1

Anti-Analyte Antibodies

Antibodies that bind to aflatoxin are produced as described in J. Langone and H. Van Vunakis, *J. Natl. Cancer Inst.* 56, 591-595 (1976); J. Groopman et al., *Proc. Natl. Acad. Sci. USA* 81, 7728-7731 (1984); G. Zhang and F. Chu, *Experientia* 45, 182-184 (1989), J. Gathumbi et al., *Lett. Appl. Microbiol* 32, 349-351 (2001), or variations thereof that will be apparent to those skilled in the art. In the alternative such antibodies are purchased from commercial sources such as Santa Cruz Biotechnology Inc., 2145 Delaware Avenue, Santa Cruz, Calif. 95060 USA.

Antibodies that bind to ergot alkaloids are produced as described in N. Hill et al., *Antibody binding of circulating ergot alkaloids in cattle grazing tall fescue*, Am. J. Vet. Res. 55, 419-424 (1994), or variations thereof that will be apparent to those skilled in the art.

Antibodies that bind to fumonisins are produced as described in J. Azcona-Olivera et al., *Applied and Environmental Microbiology* 58, 169-173 (1992), or variations thereof that will be apparent to those skilled in the art.

Antibodies that bind to trichothecene mycotoxin are produced as described in M. Abouzied et al., *Applied and Environmental Microbiology* 59, 1264-1268 (1993), or variations thereof that will be apparent to those skilled in the art.

Antibodies that bind *Staphylococcus aureus* enterotoxin are purchased from commercial sources such as Santa Cruz Biotechnology Inc., 2145 Delaware Avenue, Santa Cruz, Calif. 95060 USA.

Antibodies that bind *Staphylococcus aureus* cells are purchased from commercial sources such as Santa Cruz Biotechnology Inc., 2145 Delaware Avenue, Santa Cruz, Calif. 95060 USA.

Example 2

Antibody Immobilization

Antibodies of the Examples above are coupled to a polystyrene carrier or carrier segment as described in the Figures herein, or to a polystyrene chamber side wall portion or segment thereof as described in the Figures herein, by physical adsorption as described in W. Qian et al., *Immobilization of antibodies on Ultraflat polystyrene surfaces*, Clinical Chemistry 46, 1459-1463 (2000), or variations thereof that will be apparent to those skilled in the art.

Antibodies of the Examples above are covalently coupled to a polystyrene carrier or carrier segment as described in the Figures herein, or to a polystyrene chamber side wall portion or segment thereof as described in the Figures herein, by the method described in O Siiman et al., *Covalently Bound Antibody on Polystyrene Latex Beads*, Journal of Colloid and Interface Science, 234, 44-58 (2001), or variations thereof that will be apparent to those skilled in the art.

Antibodies of the Examples above are coupled to a polycarbonate carrier or carrier segment as described in the Figures herein, or to a polycarbonate chamber side wall portion or segment thereof as described in the Figures herein, by the method described in R. Green et al., *Radioimmunoassay on Polycarbonate Membranes*, Appl. Microbiol 27, 475-479 (1974), or variations thereof that will be apparent to those skilled in the art.

Antibodies of the Examples above are coupled to a polycarbonate carrier or carrier segment as described in the Figures herein, or to a polycarbonate chamber side wall portion or segment thereof as described in the Figures herein, by the method described in P. Hajmabadi et al., *A method for Fabrication of Polycarbonate-Based Bioactive Platforms*, Journal of Laboratory Automation, 13, 284-288 (2008), or variations thereof that will be apparent to those skilled in the art.

Example 3

Covalent Coupling of *Mycoplasma bovis* Mouse Monoclonal Antibody to Carboxy Magnetic Particles Preparation of Phosphate Buffer, 0.1 M, pH 5.0:

Phosphate Buffer Powder 0.1 M (Sigma Aldrich cat # P7994, lot #041M6108, 4.3 grams) was dissolved in distilled water (250 ml) and the pH was adjusted to 5.0 by the addition of concentrated Hydrochloric Acid.

Preparation of Spherotech Carboxy Magnetic Particle Stock Solution:

A tube was charged with 0.25 ml of Spherotech Carboxy Magnetic Particles (cat # CM-200-10, lot # AA01, 1.0% w/v, 21.4 microns, 10 ml). A magnet was applied to the bottom of the tube to pull the Carboxy Magnetic Particles to the bottom of the tube. The buffer was carefully pipetted off, the magnet removed, and the Carboxy Magnetic Particles were resuspended in 0.05 ml of Phosphate Buffer, 0.1 M, pH 5.0.

Preparation of N-(3-dimethylaminopropyl)-N-ethylcarbodiimide (EDC) Stock Solution:

A tube was charged with N-(3-dimethylaminopropyl)-N-ethylcarbodiimide hydrochloride (Sigma-Aldrich, cat # E7750, lot #079K1395V, 10 mg) and dissolved in Phosphate Buffer, 0.1 M, pH 5.0 (50 μl).

*Mycoplasma bovis* (201) Antibody was purchased from Santa Cruz Biotechnology, Inc., Cat # sc-66067, lot # F1507, 100 μg/ml. This is a mouse monoclonal $IgG_1$ raised against *Mycoplasma bovis* cells.

Covalent Coupling of *Mycoplasma bovis* Mouse Monoclonal Antibody to Carboxy Magnetic Particles:

A 1.7 ml tube was charged with Spherotech Carboxy Magnetic Particle stock solution (0.05 ml) and placed onto a magnetic separation rack for three minutes. At this point, the rust-colored Carboxy Magnetic Particles had collected on one spot on the wall of the tube. The supernatant was cautiously removed by pipette, taking care not to disturb the Carboxy Magnetic Particles that were magnetically stuck to the tube wall. The tube was removed from the rack and the Carboxy Magnetic Particles were re-suspended in 1 ml of Phosphate Buffer, 0.1 M, pH 5.0. The tube was placed onto a magnetic separation rack for three minutes. At this point, the rust-colored Carboxy Magnetic Particles had collected on one spot on the wall of the tube. The supernatant was cautiously removed by pipette, taking care not to disturb the Carboxy Magnetic Particles that were magnetically stuck to the tube wall.

The tube was charged with *Mycoplasma bovis* (201) Antibody (185 μl), and N-(3-dimethylaminopropyl)-N-ethylcarbodiimide (EDC) stock solution (19 μl). The tube was capped and placed in a rocker and rocked for two hours at room temperature. During the two hour rocking period the tube was removed and repeatedly inverted every 20 minutes to ensure thorough mixing of the reactants. Once the two hour rocking period was complete, the tube was placed onto a magnetic separation rack for three minutes. At this point, the cap was removed and the rust-colored Carboxy Magnetic Particles had collected on one spot on the wall of the tube. The supernatant was cautiously removed by pipette, taking care not to disturb the Carboxy Magnetic Particles that were magnetically stuck to the tube wall. The tube was removed from the rack and the Carboxy Magnetic Particles were suspended in Hyclone Dulbecco's Phosphate Buffered Saline (DPBS) Modified, without Calcium or Magnesium (Thermo Scientific, cat # SH30028.03, lot # AWH15873, 1 ml). The tube was placed onto a magnetic separation rack for three minutes. At this point, the Carboxy Magnetic Particles had collected on one spot on the wall of the tube. The supernatant was cautiously removed by pipette, taking care not to disturb the Carboxy Magnetic Particles that were magnetically stuck to the tube wall. The Carboxy Magnetic Particles were washed two more times with Hyclone Dulbecco's Phosphate Buffered Saline (DPBS) Modified, without Calcium or Magnesium (Thermo Scientific, cat # SH30028.03, lot # AWH15873, 1 ml).

The Carboxy Magnetic Particles were suspended in Hyclone Dulbecco's Phosphate Buffered Saline (DPBS) Modified, without Calcium or Magnesium (Thermo Scientific, cat # SH30028.03, lot # AWH15873) to bring them to a final concentration of 0.25% (w/v).

The Carboxy Magnetic Particles with *Mycoplasma bovis* Mouse Monoclonal Antibody covalently bound suspended in Hyclone Dulbecco's Phosphate Buffered Saline (DPBS) Modified without Calcium or Magnesium at a final concentration of 0.25% (w:v) is the stock solution used in the example below.

Example 4

Capturing *Mycoplasma bovis* with *Mycoplasma bovis* Mouse M Onoclonal Antibody Covalently Bound to Carboxy Magnetic Particles

*Mycoplasma bovis* culture was prepared by growing *Mycoplasma bovis* anaerobically for 7 days at 37° C.

A sterile tube was charged with *Mycoplasma bovis* culture (100 μl) and Carboxy Magnetic Particles with *Mycoplasma bovis* Mouse Monoclonal Antibody covalently bound suspended in Hyclone Dulbecco's Phosphate Buffered Saline (DPBS) Modified without Calcium or Magnesium at a final concentration of 0.25% (w:v) (50 μl). The mixture was incubated for two hours, with agitation of the mixture every 15 min. Following incubation, the tube was placed onto a magnetic separation rack for three minutes. At this point, the Carboxy Magnetic Particles had collected on one spot on the wall of the tube. The supernatant was cautiously removed by pipette to remove unbound *Mycoplasma bovis* cells.

The tube was removed from the rack and the Carboxy Magnetic Particles were suspended in Hyclone Dulbecco's Phosphate Buffered Saline (DPBS) Modified, without Calcium or Magnesium (Thermo Scientific, cat # SH30028.03, lot # AWH15873, 1 ml). The tube was placed onto a magnetic separation rack for three minutes. At this point, the Carboxy Magnetic Particles had collected on one spot on the wall of the tube. The supernatant was cautiously removed by pipette, taking care not to disturb the Carboxy Magnetic Particles that were magnetically stuck to the tube wall. This washing procedure was repeated twice.

The Carboxy Magnetic Particles with *Mycoplasma bovis* attached were resuspended in Hyclone Dulbecco's Phosphate Buffered Saline (DPBS) Modified, without Calcium or Magnesium (Thermo Scientific, cat # SH30028.03, lot # AWH15873, 50 μl). A 10 μl aliquot of the 50 μl Carboxy Magnetic Particles suspension was combined in a tube with a 0.01% Acridine Orange, pH=3.0, (10 μl) solution for staining. After incubation for 10 minutes at room temperature, 10 μl of the staining mixture was loaded onto one a flat view cell and the view cell was read under a Zeiss fluorescent microscope. *Mycoplasma bovis* organisms were observed on the surface of the beads, confirming capture thereof.

The foregoing is illustrative of the present invention, and is not to be construed as limiting thereof. The invention is defined by the following claims, with equivalents of the claims to be included therein.

That which is claimed is:

1. A device for detecting at least one analyte in a liquid sample, comprising:
   (a) a support having a chamber for receiving a liquid sample therein, wherein said chamber is an elongate chamber having a length axis and a side wall portion;
   (b) a carrier in said elongate chamber, said carrier having opposite end portions and a side portion, said carrier dimensioned to travel in said chamber along said length axis, and/or permit flow of said liquid sample in said chamber around said carrier to thereby agitate said liquid sample; and
   (c) at least one anti-analyte antibody coupled to either said carrier or to said chamber side wall portion, each at least one analyte being specifically bound by a different antibody of each of said at least one anti-analyte antibody.

2. The device of claim 1, wherein said at least one antibody comprises a plurality of different antibodies that specifically bind to different analytes of each of said at least one analyte, and wherein each of said plurality of antibodies is bound to said carrier and/or said chamber side wall portion at separate and discrete locations.

3. The device of claim 1, wherein said carrier comprises a plurality of segments coupled to one another, each of said segments having a side portion, with each of said side portions having a different antibody coupled thereto.

4. The device of claim 1, wherein said chamber side wall portion comprises a plurality of segments, each of said segments having a different antibody coupled thereto.

5. The device of claim 1, wherein said at least one antibody comprises an anti-bacterial pathogen antibody.

6. The device of claim 1, wherein said at least one antibody comprises an anti-*Mycoplasma* antibody.

7. The device of claim 1, wherein said at least one antibody comprises an anti-*Staphylococcus aureus* antibody.

8. The device of claim 1, wherein said at least one antibody comprises at least one antibody that binds to Gram negative bacteria and at least one antibody that binds to Gram positive bacteria.

9. The device of claim 1, wherein said at least one antibody comprises an anti-toxin antibody.

10. The device of claim 1, wherein said at least one antibody comprises an anti-aflatoxin antibody.

11. The device of claim 1, wherein said carrier has a density greater than, or less than, said biological fluid.

12. The device of claim 1, wherein said chamber has an internal length dimension and said carrier has an external length dimension, wherein said chamber internal length dimension is at least twice that of said carrier external length dimension.

13. The device of claim 1, wherein said chamber has an internal width dimension and said carrier has an external width dimension, wherein said chamber internal width dimension is from 10 to 30 percent greater than said carrier external width dimension.

14. The device of claim 1, wherein said chamber has a depth dimension and said carrier has thickness dimension, wherein said chamber depth dimension is from 10 to 30 percent greater than said carrier thickness dimension.

15. The device of claim 1, wherein said carrier and said chamber are configured so that said carrier cannot rotate in said chamber.

16. The device of claim 1, wherein said chamber has a total volume of from 1 ml to 10 ml, and said carrier occupies from 20 to 40 percent of said chamber volume.

17. A method for detecting at least one analyte in a liquid sample, said method comprising:
   (a) providing a device of claim 1;
   (b) adding said liquid sample to said chamber;
   (c) agitating said support in said liquid sample sufficient to bind said at least one analyte in said liquid sample to said at least one antibody; and then
   (d) detecting the presence or absence of binding of said at least one analyte to said at least one antibody.

18. The method of claim 17, wherein said detecting step comprises quantitatively detecting.

19. The method of claim 17, wherein said liquid sample comprises a biological fluid.

20. The method of claim 17, wherein said liquid sample comprises milk, whole blood, blood plasma, urine, nasal swab fluid, sputum, bronchial fluid, culture media, or a tissue homogenate.

21. The method of claim 17, wherein said liquid sample comprises milk.

22. The method of claim 17, wherein said liquid sample comprises raw whole mammalian milk.

23. A device for detecting at least one analyte in a liquid sample, comprising:
   (a) a support having a chamber for receiving a liquid sample therein, wherein said chamber is an elongate chamber having a length axis and a side wall portion;
   (b) a carrier in said elongate chamber, said carrier having opposite end portions and a side portion, said carrier dimensioned to travel in said chamber along said length axis, and/or permit flow of said liquid sample in said chamber around said carrier to thereby agitate said liquid sample, with said carrier and said chamber configured so that said carrier cannot rotate in said chamber; and wherein:
      (i) said chamber has an internal length dimension and said carrier has an external length dimension, wherein said chamber internal length dimension is at least twice that of said carrier external length dimension;
      (ii) said chamber has an internal width dimension and said carrier has an external width dimension, wherein said chamber internal width dimension is from 10 to 30 percent greater than said carrier external width dimension; and (iii) said chamber has a total volume of from 1 ml to 10 ml, and said carrier occupies from 20 to 40 percent of said chamber volume;

(c) a plurality of different antibodies that bind to different analytes, and wherein each of said plurality of antibodies is bound to said carrier and/or said chamber side wall portion at separate and discrete locations; and (d) either (i) said carrier comprises a plurality of segments coupled to one another, each of said segments having a side portion, with each of said side portions having a different antibody coupled thereto, or (ii) said chamber side wall portion comprises a plurality of segments, each of said segments having a different antibody coupled thereto.

\* \* \* \* \*